United States Patent
Monkawa et al.

(10) Patent No.: US 9,928,619 B2
(45) Date of Patent: Mar. 27, 2018

(54) DEVICE AND METHOD FOR IMAGE RECONSTRUCTION AT DIFFERENT X-RAY ENERGIES, AND DEVICE AND METHOD FOR X-RAY THREE-DIMENSIONAL MEASUREMENT

(71) Applicant: TOKYO METROPOLITAN INDUSTRIAL TECHNOLOGY RESEARCH INSTITUTE, Tokyo (JP)

(72) Inventors: Akira Monkawa, Tokyo (JP); Shoichi Nakanishi, Tokyo (JP); Shinya Abe, Tokyo (JP); Mikiya Kondo, Tokyo (JP); Koh Harada, Tokyo (JP)

(73) Assignee: Tokyo Metropolitan Industrial Technology Research Institute, Tokyo (JP)

(*) Notice: Subject to any disclaimer, the term of this patent is extended or adjusted under 35 U.S.C. 154(b) by 83 days.

(21) Appl. No.: 14/894,325

(22) PCT Filed: May 29, 2014

(86) PCT No.: PCT/JP2014/064330
§ 371 (c)(1),
(2) Date: Nov. 25, 2015

(87) PCT Pub. No.: WO2014/192889
PCT Pub. Date: Dec. 4, 2014

(65) Prior Publication Data
US 2016/0133032 A1    May 12, 2016

(30) Foreign Application Priority Data
May 29, 2013   (JP) ................................. 2013-113498

(51) Int. Cl.
*G06T 11/00*     (2006.01)
*G01N 23/04*    (2018.01)
(Continued)

(52) U.S. Cl.
CPC ............ *G06T 11/008* (2013.01); *G01B 15/04* (2013.01); *G01N 23/046* (2013.01); *G06K 9/52* (2013.01);
(Continued)

(58) Field of Classification Search
CPC ........ A61B 6/032; A61B 6/4241; A61B 6/482
See application file for complete search history.

(56) References Cited

U.S. PATENT DOCUMENTS

| | | | |
|---|---|---|---|
| 2002/0044631 | A1 | 4/2002 | Graumann et al. |
| 2004/0234025 | A1 | 11/2004 | Schroeder et al. |

(Continued)

FOREIGN PATENT DOCUMENTS

| | | | |
|---|---|---|---|
| EP | 1380263 A1 | 1/2004 | |
| EP | 1531426 A1 | 5/2005 | |

(Continued)

OTHER PUBLICATIONS

Yu Kuang et al., "Medical Physics Letter—Development of XFCT Imaging Strategy for Monitoring the Spatial Distribution of Platinum-based Chemodrugs: Instrumentation and Phantom Validation", Medical Physics, vol. 40, No. 3, Mar. 2013.

(Continued)

*Primary Examiner* — Hoon Song
(74) *Attorney, Agent, or Firm* — Sheppard, Mullin, Richter & Hampton LLP

(57) ABSTRACT

A device and a method for image reconstruction at different X-ray energies that make it possible to achieve image reconstruction with higher accuracy. A device for image reconstruction at different X-ray energies includes: an X-ray source 1 that irradiates a specimen to be imaged 2 with X-rays; an energy-dispersive detector 4 that detects a characteristic X-ray emitted from the specimen to be imaged 2; a signal processor that quantifies the peak of the character- (Continued)

istic X-ray detected by the detector 4; and an image reconstruction device that reconstructs an image on the basis of a signal from the signal processor.

9 Claims, 11 Drawing Sheets

(51) Int. Cl.
    *G06K 9/52*     (2006.01)
    *G06T 7/00*     (2017.01)
    *H04N 5/232*     (2006.01)
    *H04N 13/00*     (2018.01)
    *H04N 13/02*     (2006.01)
    *G01B 15/04*     (2006.01)

(52) U.S. Cl.
    CPC ....... *G06T 7/0004* (2013.01); *H04N 5/23293* (2013.01); *H04N 13/004* (2013.01); *H04N 13/0203* (2013.01); *G01N 2223/076* (2013.01); *G01N 2223/408* (2013.01); *G01N 2223/423* (2013.01); *G06T 2207/10081* (2013.01); *G06T 2207/10116* (2013.01); *G06T 2207/30108* (2013.01)

(56) References Cited

U.S. PATENT DOCUMENTS

| | | |
|---|---|---|
| 2005/0123089 A1 | 6/2005 | De Man |
| 2006/0002504 A1 | 1/2006 | De Man et al. |
| 2006/0093082 A1 | 5/2006 | Numata et al. |
| 2009/0310736 A1 | 12/2009 | Ziegler et al. |
| 2013/0287175 A1* | 10/2013 | Nagai ................ A61B 6/4233 378/91 |

FOREIGN PATENT DOCUMENTS

| | | |
|---|---|---|
| EP | 1933170 A1 | 6/2008 |
| JP | H03108645 A | 5/1991 |
| JP | H11281747 A | 10/1999 |
| JP | 2006017714 A | 1/2006 |
| JP | 2006125960 A | 5/2006 |
| JP | 2006329917 A | 12/2006 |
| JP | 2008070219 A | 3/2008 |
| JP | 2009543603 A | 12/2009 |

OTHER PUBLICATIONS

International Application No. PCT/JP2014/064330, International Search Report dated Sep. 2, 2014.

Nishihata, Takahiro et al., "Sinogram-based Beam Hardening Correction using Volume Conservation for Single-material Objects," The Japan Society for Precision Engineering Autumn Meeting, Sep. 2012.

Suzuki, Shigehito, "Various Methods of Iterative Least-Squares Image Reconstruction for Emission Tomography," Japanese Journal of Medical Physics, vol. 19, No. 3, pp. 193-204, Sep. 30, 1999.

Lange, Kenneth et al., "EM Reconstruction Algorithms for Emission and Transmission Tomography," Journal of Computer Assisted Tomography, New York, NY, vol. 8, No. 2, pp. 306-316, Apr. 1984.

* cited by examiner

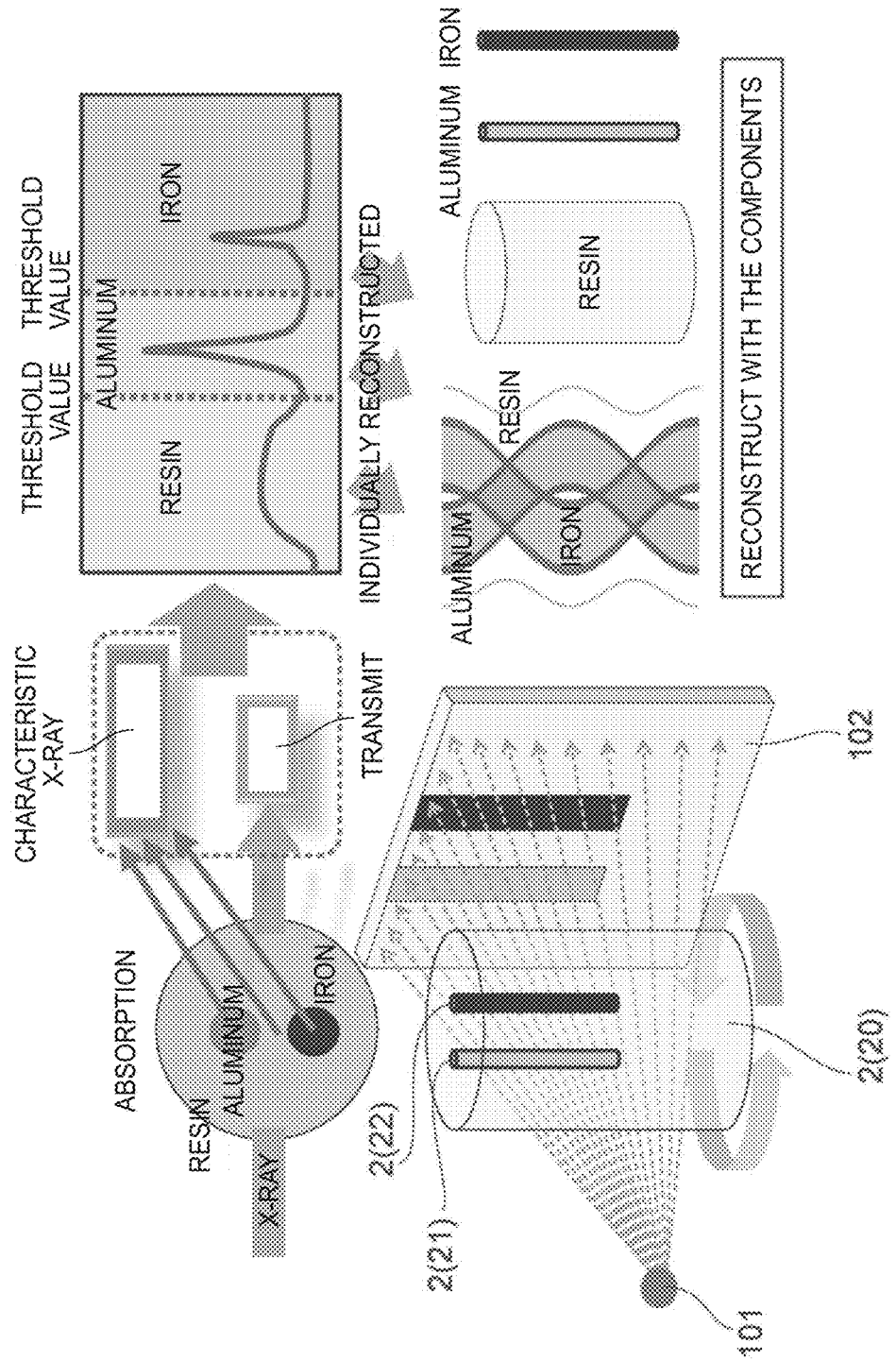

DEVICE AND METHOD FOR IMAGE RECONSTRUCTION AT DIFFERENT X-RAY ENERGIES, AND DEVICE AND METHOD FOR X-RAY THREE-DIMENSIONAL MEASUREMENT

CROSS REFERENCE TO RELATED APPLICATIONS

This application is a National Phase application under 35 U.S.C. § 371 of PCT Application PCT/JP2014/064330, filed May 29, 2014, which claims priority to Japanese Patent Application No. 2013-113498, filed May 29, 2013, which are all hereby incorporated by reference.

TECHNICAL FIELD

The present invention relates to a device and a method for image reconstruction at different X-ray energies, and a device and a method for X-ray three-dimensional measurement.

BACKGROUND ART

An X-ray computed tomography ("CT") device is capable of obtaining a three-dimensional image including an internal structure of an object by carrying out reconstruction processing on the images of the object taken with X-rays from various directions. Hitherto, the features of the X-ray CT device have been used to observe minute internal defects, such as a void and a crack, in a metal part or a resin part or the like, to measure the complicated internal shape of an electronic part, and to analyze a cause of a failure. See Patent Documents 1 to 4, below.)

With the recent advance of digital technologies, an attempt to use an X-ray CT device as the core of a digital engineering system has begun. The digital engineering system represents the technology for integrating a sophisticated computer-assisted design ("CAD")/computer-assisted modeling ("CAM") system, a three-dimensional formative system, and a three-dimensional measurement system to achieve efficiency and high quality throughout the whole process from development to manufacture. Combining these technologies makes it possible to repeatedly design and make prototypes without making molds and to commercialize products in a short time and at low cost. A reduced risk in development is expected by sharing accurate and complete production and technological data.

As a three-dimensional measurement system, a digitizer, a light-section method and the like have been proposed. However, it is extremely difficult to measure the internal shape of an object to be measured by the foregoing methods although the methods permit accurate measurement of surface shapes. In contrast to the measurement methods, there has been proposed an ultrasonic diagnosis that is capable of determining the presence of an internal space. However, it is also difficult to accurately grasp an internal shape by the ultrasonic diagnosis. For these reasons, an X-ray CT device is expected as the only three-dimensional measurement system capable of also determining an internal structure.

CITATION LIST

Patent Document

Patent Document 1: JP2006-125960A
Patent Document 2: JP2006-329917A
Patent Document 3: JP2008-70219A
Patent Document 4: JPH11-281747A

SUMMARY

Technical Problem

How to improve the accuracy of measurement of CT data is a crucial factor in using an X-ray CT device as a three-dimensional measurement system. In the case of a CT image, an artifact, a noise, a blur or the like occurs depending on measurement conditions or in a reconstruction process, resulting in dimensional differences between an actual specimen and an obtained image. An artifact is caused by, for example, a considerable difference in absorption rate in the case where metals are scattered in a resin, or in the case where the X-ray transmission distance significantly varies according to an imaging direction. One of the causes for the dimensional difference between the specimen and the image attributable to such an artifact or the like is that the conventional CT image reconstruction method does not give consideration to a mass attenuation coefficient (=linear attenuation coefficient) μ, which differs for each composition contained in a specimen.

An X-ray that has passed through a material attenuates due to the interactions with the material, typically represented by photoelectric absorption, Compton scattering, and electron pair creation. When an X-ray having a single energy level passes through a material having a thickness t, a relationship represented by the following expression holds between an incident X-ray intensity (=the number of incident photons) $I_0$ and a transmitted X-ray intensity I:

$$I = I_0 \exp(-\mu t) \quad (1)$$

Expression (1) holds for imaging with a monochromatic X-ray. However, in the case of a continuous X-ray used for actual measurement, expression (1) does not hold, because the mass attenuation coefficient changes according to the energy of an incident X-ray. For the continuous X-ray, the transmitted X-ray intensity I is represented by the integration system of energy indicated by expression (2) given below.

$$I = \int I_0(E) \exp(-\mu(E)t) dE \quad (2)$$

To accurately reconstruct an image, expression (2) should be used for the calculation. However, because of the problems with the performance of a detector and the amount of calculation, a currently used X-ray CT device assumes that the continuous X-ray is a monochromatic X-ray and carries out the calculation for reconstruction.

Means for meeting such a challenge include a method using a monochromatic X-ray and a dual energy scanning method, in which data is gathered at different tube voltages. However, the irradiation dose of the monochromatic X-ray inconveniently decreases due to the monochromatization, thus limiting its use to specific facilities where a sufficient dose of radiation can be obtained. Further, the dual energy scanning method requires a plurality of times of imaging at different tube voltages, leaving some challenges to be met, such as positional deviations and prolonged measurement time.

Further, a conventional X-ray CT device for three-dimensional measurement is known to be incapable of maintaining dimensional accuracy in the measurement of an actual object to be measured whereas it is capable of maintaining a certain level of dimensional accuracy when a particular measurement standard, e.g. a calibration jig, is used. This is because, for example, the resolution of an X-ray detector is lower than the actual measurement accuracy, or the shapes and the materials of an actual object to be measured vary. Hence, there has been a demand for developing a technique for correcting images acquired by an X-ray CT device.

An object of the present invention is to provide a device and a method for image reconstruction at different X-ray energies and a device and a method for X-ray three-dimensional measurement that make it possible to achieve highly accurate image reconstruction by removing an artifact or the like, which has hitherto been a problem, by correction.

Solution to Problem

To this end, provided is a device for image reconstruction at different X-ray energies, including, for example: an X-ray source that irradiates a specimen to be imaged with X-rays; an energy-dispersive detector that detects a characteristic X-ray emitted from the specimen to be imaged; a signal processor that quantifies the peak of the characteristic X-ray detected by the detector; and an image reconstruction device that reconstructs an image on the basis of a signal from the signal processor.

Further, provided is a method for image reconstruction at different X-ray energies including the steps of: irradiating a specimen to be imaged with X-rays; detecting a characteristic X-ray emitted from the specimen to be imaged by an energy-dispersive detector; quantifying the peak of the detected characteristic X-ray; and reconstructing an image on the basis of quantified data of the characteristic X-ray peak.

Further, provided is an X-ray three-dimensional measurement device including: an image acquisition device that acquires an X-ray CT image of an object to be measured on a three-dimensional coordinate axis; an actual measurement device that actually measures a three-dimensional shape of the object to be measured on the three-dimensional coordinate axis; and an image correction device that corrects the X-ray CT image such that a sinogram of the X-ray CT image of the object to be measured which has been acquired by the image acquisition device converges to a sinogram of a three-dimensional shape of the object to be measured which has been actually measured by the actual measurement device.

Further, provided is an X-ray three-dimensional measurement method including: an image acquisition step of acquiring an X-ray CT image of an object to be measured on a three-dimensional coordinate axis; an actual measurement step of actually measuring a three-dimensional shape of the object to be measured on the three-dimensional coordinate axis; and an image correction step of correcting the X-ray CT image such that a sinogram of the X-ray CT image of the object to be measured which has been acquired in the image acquisition step converges to a sinogram of a three-dimensional shape of the object to be measured which has been actually measured in the actual measurement step.

Further, provided is an X-ray three-dimensional image correction program for causing a computer to carry out an image correction step of correcting an X-ray CT image such that a sinogram of the X-ray CT image of an object to be measured which has been acquired on a three-dimensional coordinate axis converges to a sinogram of the three-dimensional shape of the object to be measured which has been actually measured on the three-dimensional coordinate axis.

BRIEF DESCRIPTION OF DRAWINGS

FIG. 20 presents explanatory diagrams illustrating an example in which the correction of an X-ray CT image by using sinograms is applied to the image reconstruction at different X-ray energies.

DESCRIPTION OF EMBODIMENTS

<Device and Method for Image Reconstruction at Different X-Ray Energies>

Figure 1B:
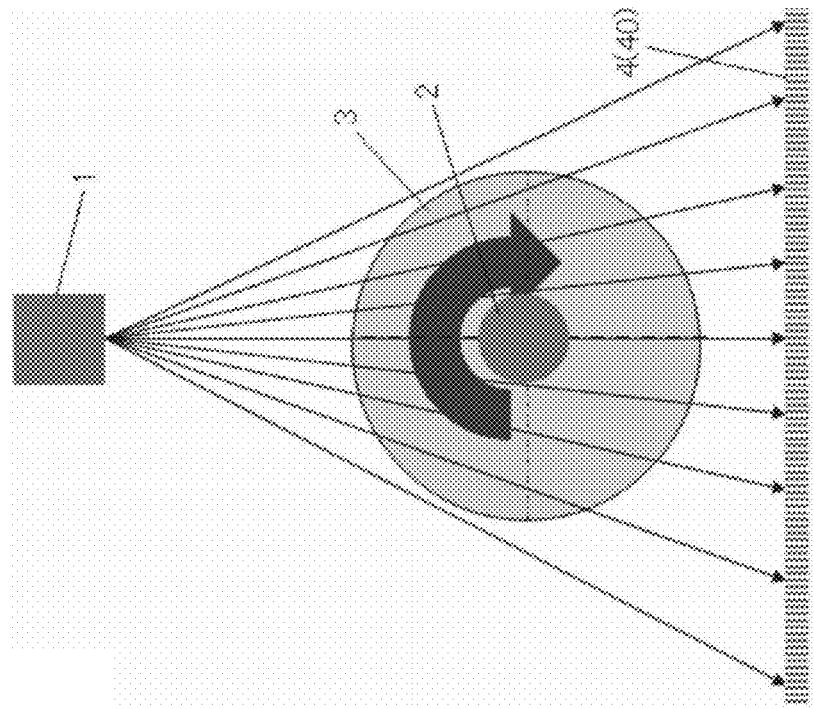
FIG. 1(a) and FIG. 1(b) are a side view and a plan view, respectively, of a device for image reconstruction at different X-ray energies.
Figure 1A:
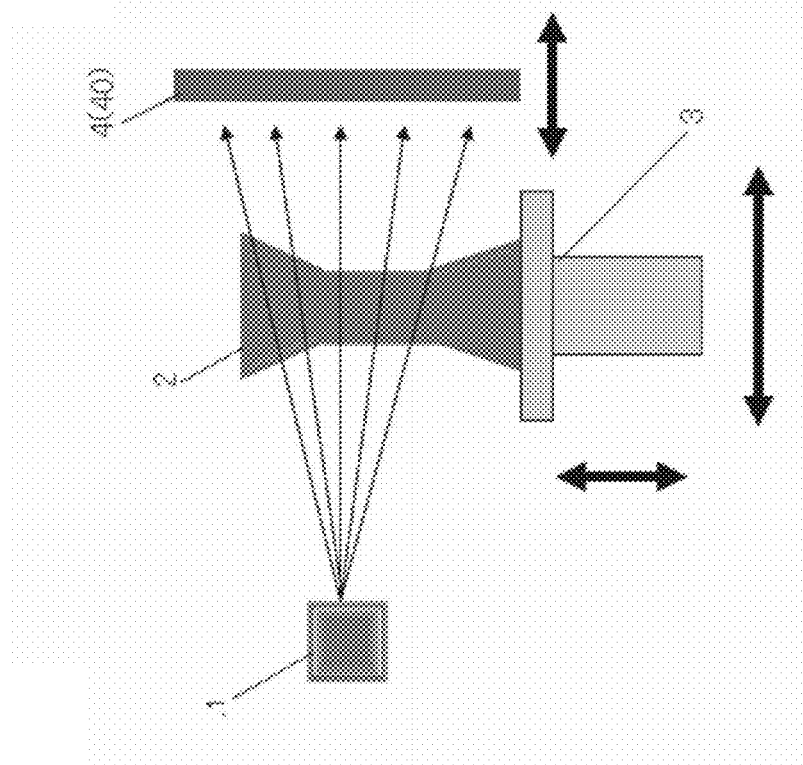
Figure 2:
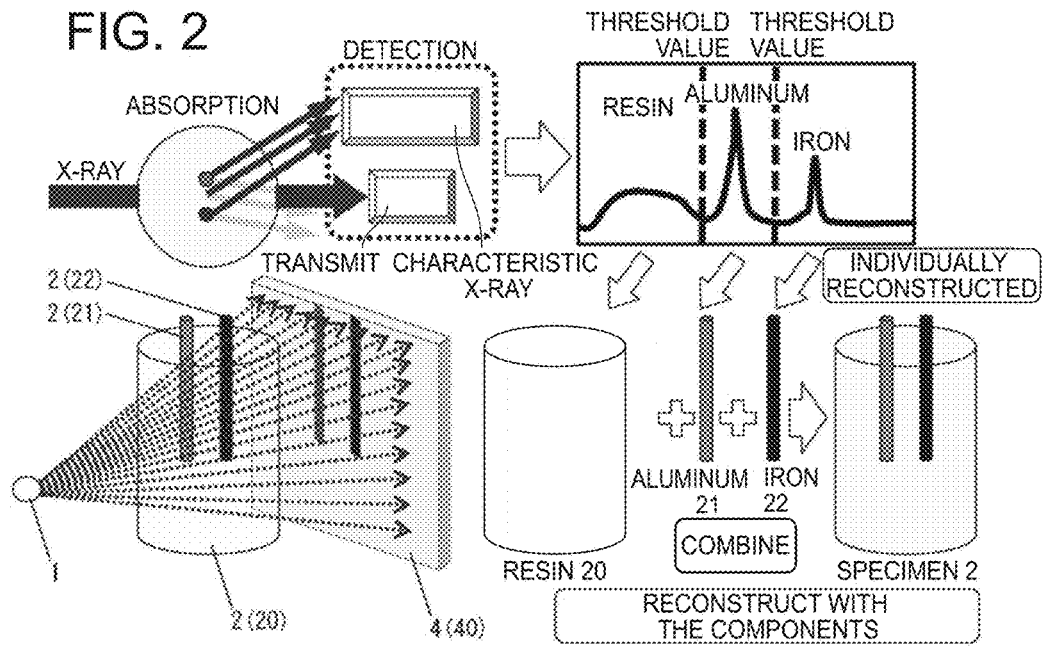
FIG. 2 is a diagram for explaining the image reconstruction at different X-ray energies.

The FIGS. 1(a) and 1(b) are diagrams illustrating an example of the configuration of a device for image reconstruction at different X-ray energies. FIG. 2 is a diagram for explaining specific image reconstruction at different X-ray energies by the device.

It is desirable to identify the types of materials contained in a specimen to be imaged 2, in addition to a change in the amount of transmission used in normal X-ray CT imaging. In order to identify the types of materials, characteristic X-rays emitted when irradiating a specimen 2 with the X-rays from an X-ray source 1 are detected by an energy-dispersive detector 4, and the information of the elements constituting the specimen to be imaged 2 and the concentrations of the elements is acquired from the energy peaks of the characteristic X-rays.

Figure 3A:
FIG. 3(a) and FIG. 3(b) are front views illustrating examples of a detector.
Figure 3B:
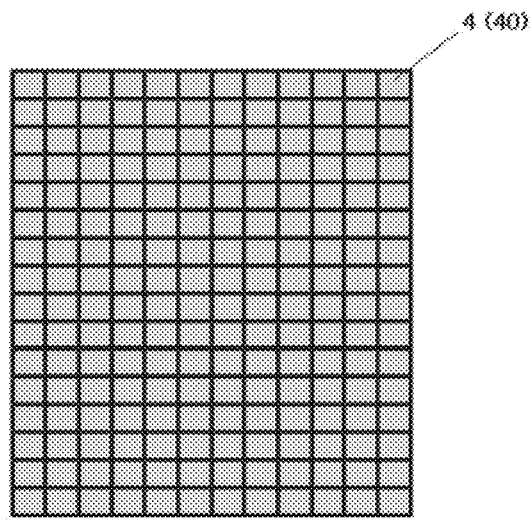

The detector 4 having energy dispersion power may include a plurality of sub-detectors 40 arranged in a line or panel formation, as illustrated in FIGS. 3(a) and 3(b). The sub-detectors 40 are desirably configured to have a construction for preventing the influences of scattered rays by shielding the sub-detectors 40 against each other with a shielding material, such as a lead or tungsten material. Preferably, each of the sub-detectors 40 is capable of acquiring the characteristic X-ray from each element obtained when the specimen to be imaged 2, which is composed of a plurality of elements, is irradiated with X-rays as a radiation energy spectrum by photon counting. Such a detector may be a semiconductor detector of cadmium telluride (CdTe), zinc cadmium sulfide telluride (CdZnTe) or the like, or a scintillation detector of cesium iodide (CsI), sodium iodide (NaI) or the like.

If the sub-detectors 40 are arranged in the line formation (FIG. 3(a)), then only one section of the specimen 2 disposed between the X-ray source 1 and the detector 4 is imaged while rotating the specimen 2, which is disposed between the X-ray source 1 and the detector 4, by a drive mechanism 3. Each time one section is imaged, the stage of the specimen is physically moved up or down to stack the tomograms thereby to acquire a three-dimensional image. The drive mechanism 3 is capable of rotating the stage on which the specimen 2 is placed by 360 degrees and translationally moving the stage in an X direction, in which the X-ray source 1 and the detector 4 are connected, in a Y direction orthogonal to the X direction, and in a vertical Z direction.

If the sub-detectors 40 are arranged in the panel formation (FIG. 3(b)), then a transparent image is acquired while rotating the specimen 2 by the drive mechanism 3, and then a three-dimensional image is acquired by reconstruction calculation. When the transparent image is acquired for each rotational angle of the specimen 2, the characteristic X-ray spectrum data for each pixel is acquired at the same time.

Figure 4:
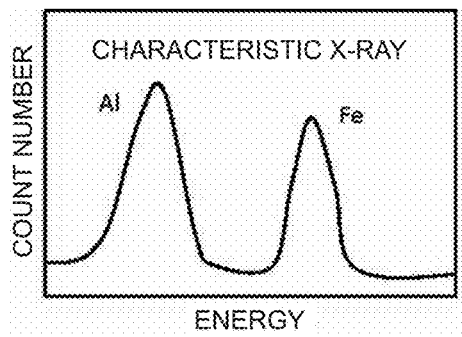
FIG. 4 is a diagram illustrating an example of a characteristic X-ray.

If the specimen 2 contains a plurality of materials, then a radiation energy spectrum having peaks corresponding to the types of elements will be obtained. The example illustrated in FIG. 4 indicates a spectrum having the peaks corresponding to aluminum (Al) and iron (Fe).

FIG. 2 illustrates a more specific example of the specimen 2, which is a specimen containing two types of scattered metals, namely, aluminum 21 and iron 22, in a resin 20. The characteristic X-rays emitted from the specimen 2 irradiated with the X-rays from the X-ray source 1 are detected as a radiation energy spectrum by photon counting performed by the detector 4, which is, for example, the foregoing semiconductor detector or scintillation detector. The detected spectrum exhibits the peaks of the aluminum and the iron, as with the one illustrated in FIG. 4.

The obtained characteristic X-ray peaks are quantified by a signal processor (not illustrated). In the example illustrated in FIG. 2, the peak intensities of the aluminum 21 and the iron 22 are quantified on the basis of energy threshold values set in advance to allow the aluminum 21 and the iron 22 to be distinguished from the resin 20 in the specimen 2. This makes it possible to acquire a transparent image of only the aluminum 21 based on the spectrum quantified data between an upper limit value and a lower limit value, and a transparent image of only the iron 22 based on the spectrum quantified data which is larger than the upper limit value. A transparent image of the resin 20 is also acquired on the basis of the spectrum quantified data which is smaller than the lower limit value.

Then, the transparent images obtained as described above are subjected to reconstruction processing performed by an image reconstruction device (not illustrated), and reconstruction calculation for each energy level is carried out.

Figure 5:
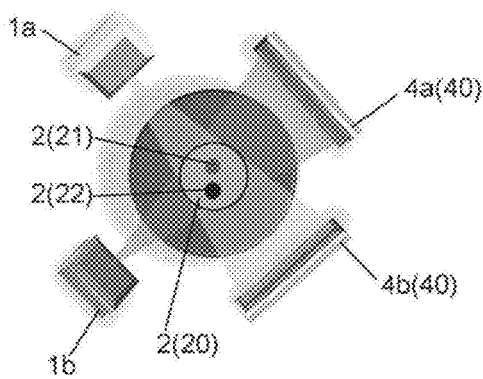
FIG. 5 is a diagram for explaining a dual energy method.
Figure 6:
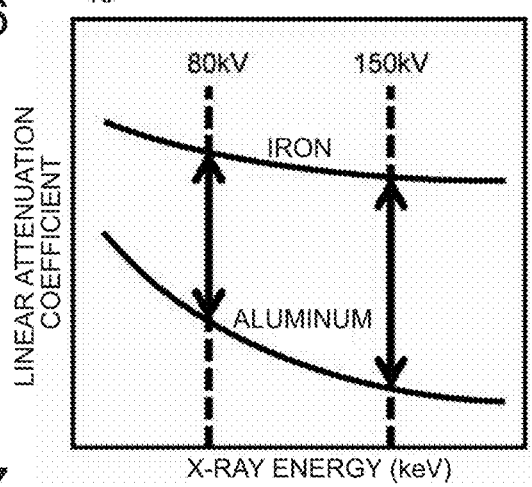
FIG. 6 is a diagram illustrating an example of a linear attenuation curve.

The reconstruction calculation will be further described. If, for example, the foregoing artifact occurs due to a considerable difference in absorption rate as in the case where metals are scattered in a resin, then the linear attenuation curve of each element of the specimen 2 is determined and ideal calculation $I=I_0 \exp^{-t}(\mu_1+\mu_2+\mu_3+ \ldots +\mu_n)$ is carried out. This makes use of the fact that the mass attenuation coefficient varies according to photon energy. More specifically, as illustrated in FIG. 5, two or more different tube voltages are used, e.g. X-ray sources 1a and 1b of tube voltages that are different from each other, are used to detect the characteristic X-ray peak of each element of the specimen 2 by detectors 4a and 4b corresponding to the X-ray sources 1a and 1b, respectively. FIG. 6 illustrates the example of the linear attenuation coefficient curves of the iron and the aluminum in the case where an X-ray source of 80 kV and an X-ray source 1b of 150 kV are used.

Figure 7:
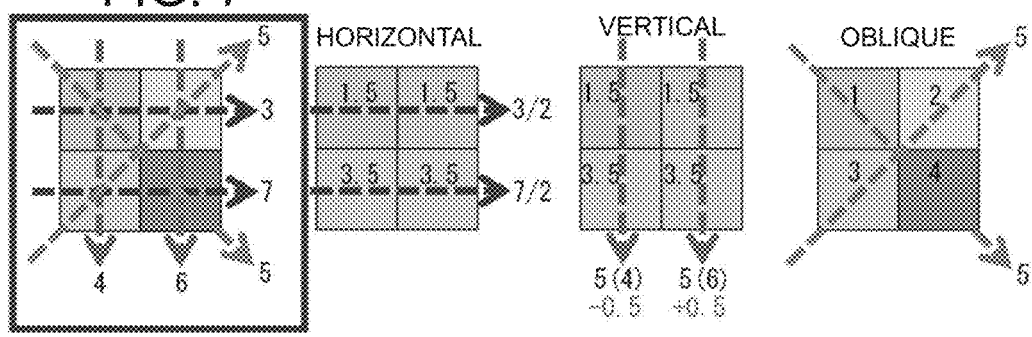
FIG. 7 is a diagram for explaining a sequential approximate reconstruction method.

Further, if an artifact occurs because a specimen has a complicated shape in which the X-ray transmission distance significantly varies depending on the imaging direction, then the sequential approximate reconstruction method illustrated in FIG. 7 is preferably used. According to the sequential approximate reconstruction method, an actual measurement value and an assumed value are compared and a correction is made each time. An artifact can be removed by repeating the correction until the difference between the actual measurement value and the assumed value falls within an allowable error range set in advance.

It is needless to say that, other than the sequential approximate method, various algorithms can be used, such as the method of all possible combinations (a brute force search), a greedy method, a hill climbing method, an annealing method, a backpropagation method, a genetic algorithm, genetic programming, an evolution strategy, and evolutionary programming.

Hence, in the image reconstruction, combining the energy sorting by the threshold value processing or the like and the artifact correction by the sequential approximate reconstruction or the like makes it possible to acquire an image from which noises, such as an artifact attributable to a plurality of materials or elements and an artifact attributable to a complicated shape, have been removed.

Although not illustrated, the signal processor and the image reconstruction device are composed of hardware, such as a computer, and software, such as programs installed in the hardware. More specifically, for example, when a program for carrying out the signal processing and the image reconstruction processing mentioned above is read into a computer via a communication medium, such as the Internet, or a memory medium, such as a USB memory, various types of processing are executed by an arithmetic processing unit, such as a CPU, or a storage unit, such as a memory. Various types of data required for the execution are supplied through an input unit or a communication unit, as necessary, and result data is output through an output unit or a display unit.

Figure 8A:
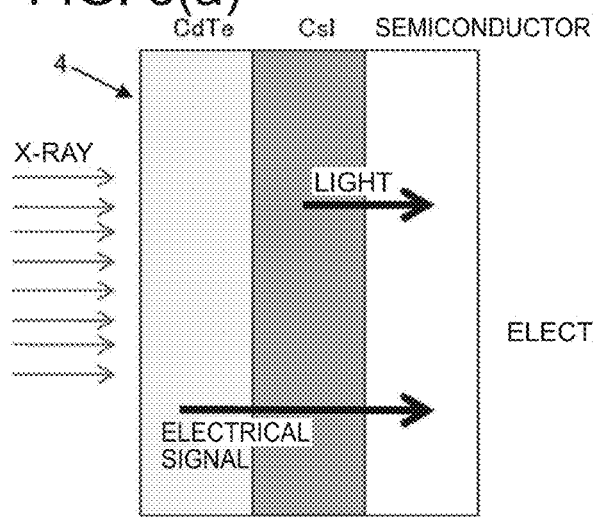
FIG. 8(a) is a sectional view illustrating another example of the detector.
Figure 8B:
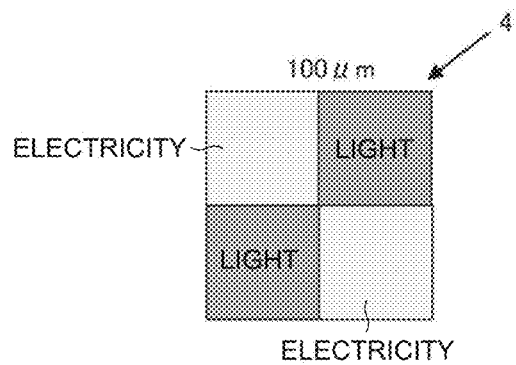
FIG. 8(b) is a front view illustrating yet another example of the detector.

FIGS. 8(a) and 8(b) illustrate a detector, which combines a semiconductor detector and a scintillation detector, as another embodiment of the energy-dispersive detector. The compound detector illustrated in FIG. 8(a) has a CdTe semiconductor detector, which directly converts X-rays to electrons, at the X-ray incidence side thereof, and also has a scintillator using CsI, which converts X-rays to light, and a photodiode or a photomultiplier tube, which uses a semiconductor, such as Ge, Si or the like, and converts light to electric signals, at the rear side thereof. The locations of the CdTe semiconductor detector and the CsI scintillator may be reversed such that X-rays enter and pass through the CsI scintillator first and then reach the CdTe semiconductor detector. In the compound detector illustrated in FIG. 8(b), a semiconductor detector of CdTe or the like, which is capable of detecting an electric signal on one pixel, and a scintillation detector of CsI or the like, which is capable of detecting light, are alternately arranged in a chessboard pattern. These arrangements make it possible to simultaneously acquire sorted energies and X-ray absorption values (CT values), thus allowing the entire device to have a simpler configuration and a reduced size.

Figure 9A:
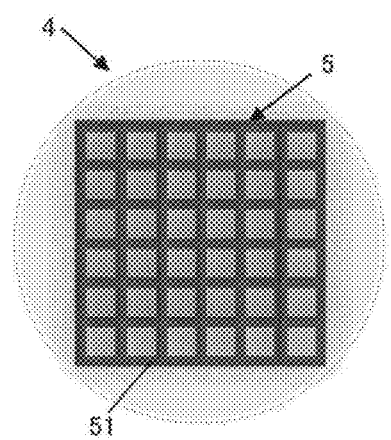
FIG. 9(a) and FIG. 9(b) are a front view and a sectional view, respectively, of still another example of the detector.
Figure 9B:
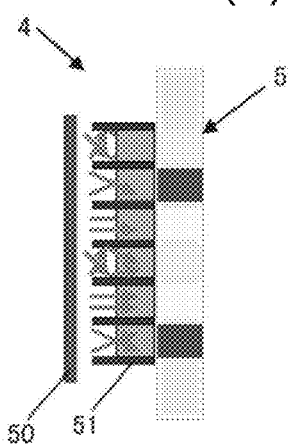
Figure 10:
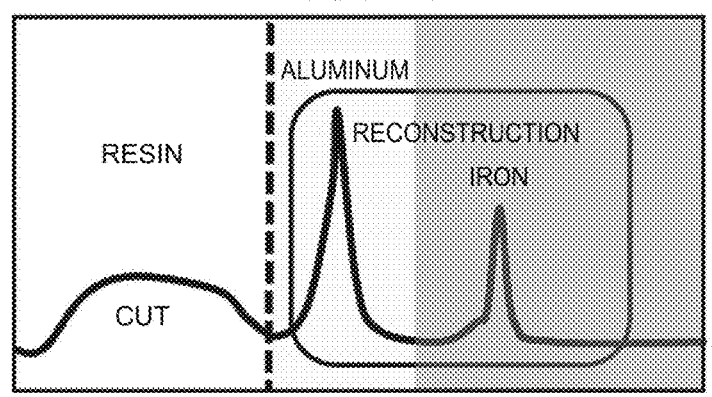
FIG. 10 is a diagram for explaining the sorting of energies by a filter in the example illustrated in FIG. 9.

FIGS. 9(a) and 9(b) illustrate an embodiment of a detector adapted to sort energies by using a filter. In the configuration, a metal filter 50 is provided in the stage before a CCD camera 5 serving as a detector (refer to FIG. 9(b); not illustrated in FIG. 9(a)), and partitions 51 are provided for individual pixels to prevent rays from scattering. With this arrangement, as illustrated in FIG. 10, an energy region corresponding to, for example, the resin constituting the specimen 2 (refer to FIG. 2) can be cut off by the metal filter 50 properly selected in advance, so that only the specimen constituent elements exhibiting high energies, namely, the aluminum and the iron in this example, can be extracted. After the extraction, the reconstruction processing described above is carried out.

The techniques described above make it possible to image the material density of a region of interest and the characteristics of the texture. An artifact, which has hitherto been a problem, can be eliminated by correction, thus allowing a three-dimensional image with higher accuracy to be obtained. Further, the three-dimensional distribution information on an element contained in a specimen to be measured can be also acquired. This is expected to improve the CT measurement technique, achieve an advance in the digital engineering technology, and also to be applied to the field of high-accuracy simulations.

<Device and Method for X-Ray Three-Dimensional Measurement>

Figure 11:
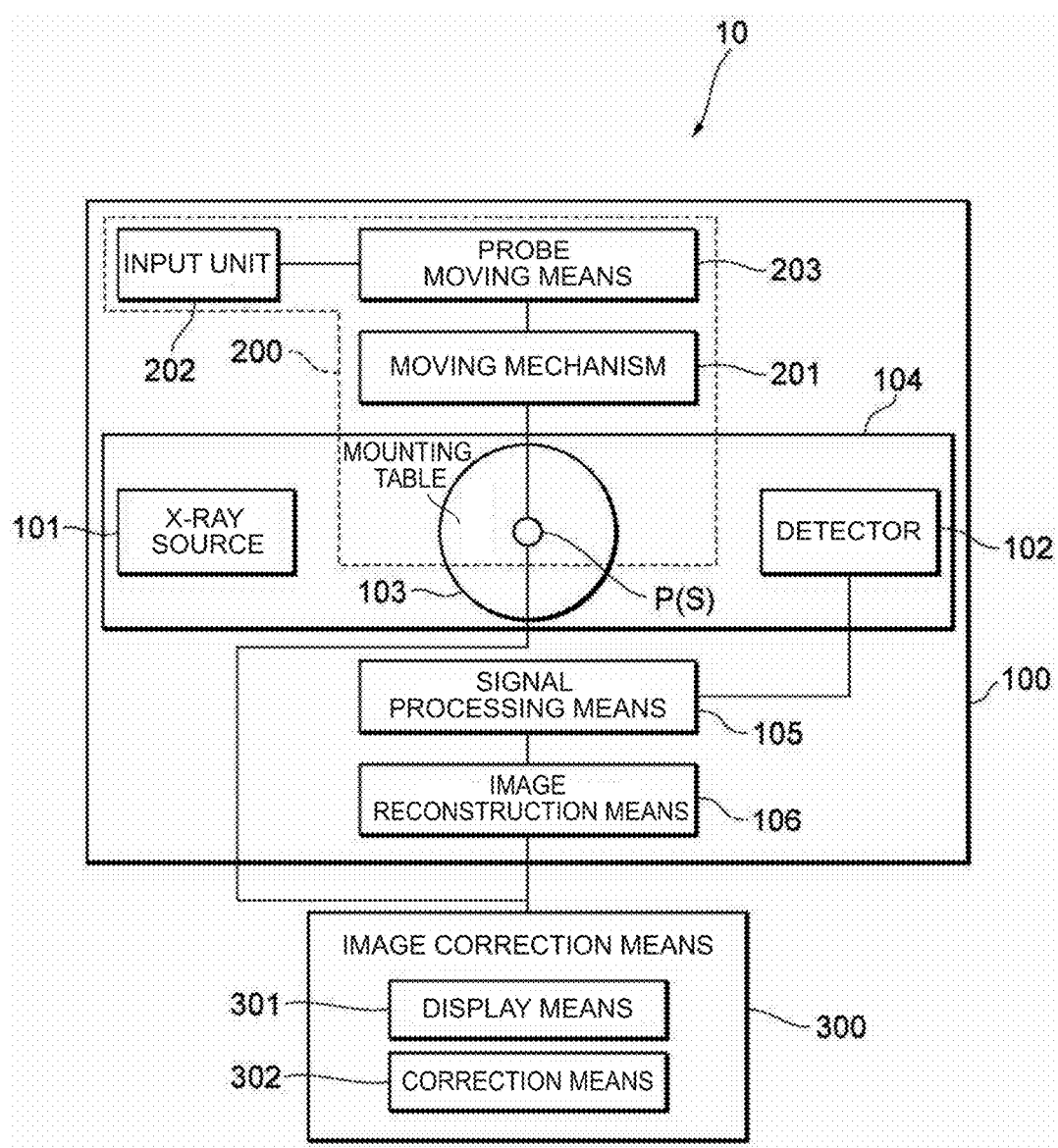
FIG. 11 is a block diagram for explaining the functional configuration of an X-ray three-dimensional measurement device.
Figure 12:
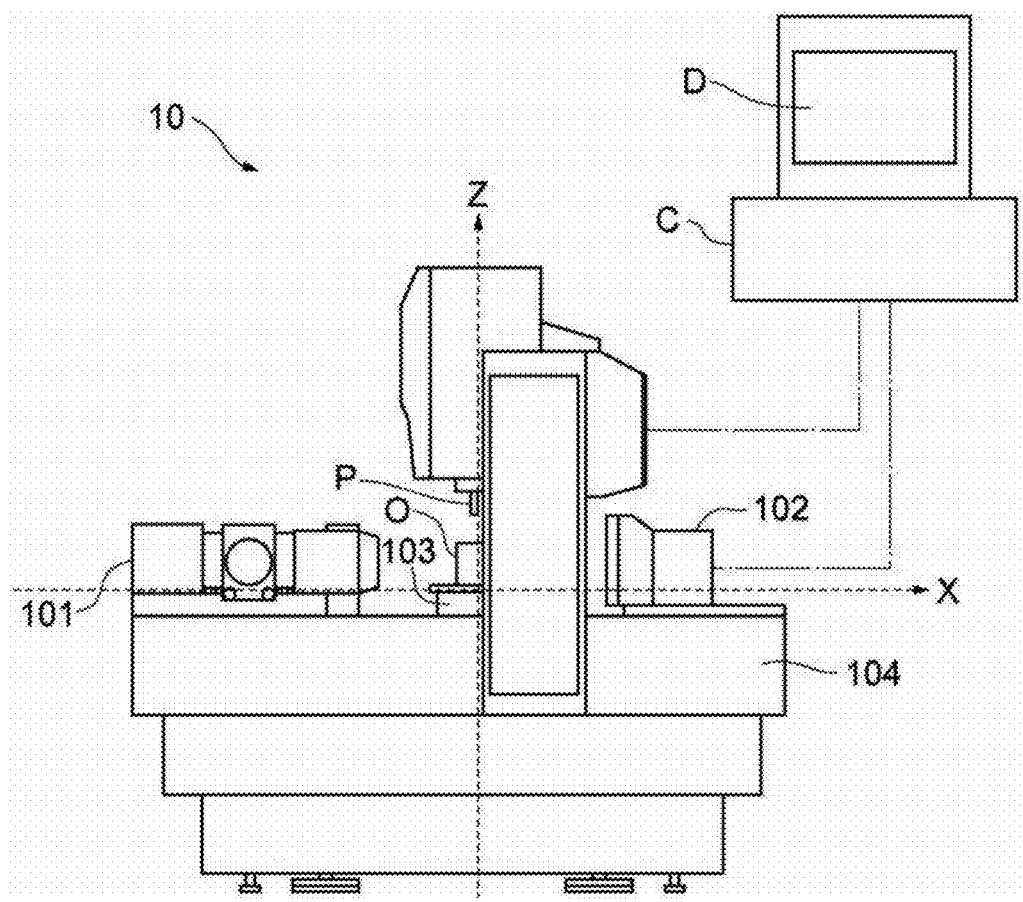
FIG. 12 is a side view of the X-ray three-dimensional measurement device.
Figure 13:
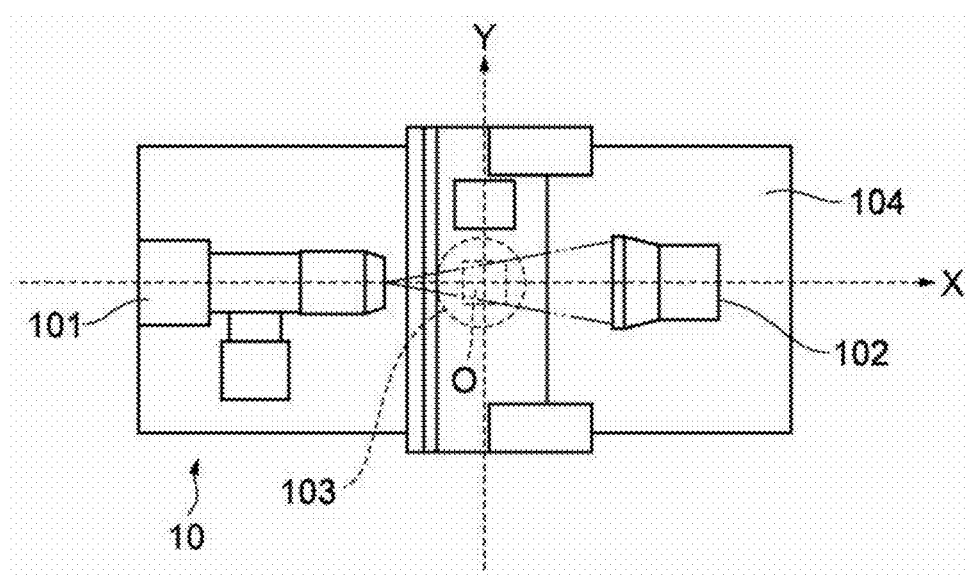
FIG. 13 is a plan view of the X-ray three-dimensional measurement device.

Referring now mainly to FIG. 11 to FIG. 13, the configuration of an X-ray three-dimensional measurement device 10 will be described. As illustrated in FIG. 11, the X-ray three-dimensional measurement device 10 includes an image acquisition device 100 for acquiring an X-ray CT image of an object to be measured O on a three-dimensional coordinate axis, an actual measurement device 200 for actually measuring the three-dimensional shape of the object to be measured O on the three-dimensional coordinate axis, and an image correction device 300 for correcting the X-ray CT image of the object to be measured O which has been acquired by the image acquisition device 100, according to the three-dimensional shape of the object to be measured O which has been actually measured by the actual measurement device 200.

The image acquisition device 100 irradiates the object to be measured O with X-rays to detect the projection data for each rotational angle of the object to be measured O, thereby acquiring the X-ray CT image of the object to be measured O on a predetermined three-dimensional coordinate axis. For this purpose, the image acquisition device 100 has, for example, an X-ray source 101 that emits X-rays, a detector 102 that detects the characteristic X-ray passing through the object to be measured O, a mounting table 103 which is disposed between the X-ray source 101 and the detector 102 and on which the object to be measured O is set, a common stage 104 for installing the X-ray source 101, the detector 102 and the mounting table 103 thereon, a signal processor 105 that quantifies the amount of the characteristic X-ray (the peak of the characteristic X-ray) measured by the detector 102, and an image reconstruction device 106 that reconstructs an image on the basis of the quantified data obtained by the signal processor.

For the detector 102, a flat panel detector, a CdTe detector or the like may be adopted. The mounting table 103 is configured to rotate about a predetermined rotation axis by a moving mechanism, which is not illustrated, and to linearly move along an axis orthogonal to the rotation axis. The mounting table 103 is preferably composed of granite or a ductile cast iron, which has high stiffness. The center of the three-dimensional coordinate axis (XYZ axis) used in the image acquisition device 100 refers to the position of the center of the common stage 104 as observed in a planar view and the center is disposed above the upper surface of the common stage 104 by a predetermined height, as illustrated in FIG. 12 and FIG. 13.

The signal processor 105 and the image reconstruction device 106 are composed of hardware, such as a computer C, and software, such as a program, installed in the hardware. More specifically, when programs for the signal processor 105 and the image reconstruction device 106 are read into the computer C via a communication medium, such as the Internet, or a memory medium, such as a USB memory, various types of processing are executed by an arithmetic processing unit, such as a CPU, or a storage unit, such as a memory. Various types of data required for the execution are supplied through an input unit or a communication unit, as necessary, and result data is output through an output unit or a display unit (e.g. a display screen D).

As with a correction device 302, which will be discussed later, the image reconstruction device 106 in the present embodiment uses the maximum likelihood estimation and expectation-maximization reconstruction method (hereinafter referred to as "the ML-EM reconstruction method") in the sequential approximate reconstruction method to reconstruct the X-ray CT image of the object to be measured O on the basis of the quantified data of the detected amount of the X-rays. The image reconstruction device 106 may reconstruct the image by using a different algorithm (e.g. a filtered backprojection method, an addition type ART method, a multiplication type ART method, a SIRT method, a gradient method, a steepest descent method, a conjugate gradient method, a MAP-EM method, or a convex method).

A linear scale may be disposed between the X-ray source 101 and the detector 102. This makes it possible to accurately determine the position of the mounting table 103, so that the X-ray CT image of the object to be measured O can be accurately acquired.

The actual measurement device 200 is a bridge type device having a probe P, as illustrated in FIG. 12 and FIG. 13, and actually measures the three-dimensional shape of the object to be measured O on a predetermined three-dimensional coordinate axis. The three-dimensional coordinate axis used by the actual measurement device 200 is the same as the three-dimensional coordinate axis used by the image acquisition device 100.

The three-dimensional coordinate axis (the origin of the probe P) is set automatically or by an operator so as to establish the positional relationship among the object to be measured O, the image acquisition device 100 and the probe P of the actual measurement device 200. The setting method may be, for example, the method described in JP2012-

137301A, in which a gauge is used to match the central coordinate of a sphere on the X-ray CT image of the gauge and the central coordinate of the ball of the gauge measured by the probe P of the actual measurement device 200; however, the setting method is not limited thereto.

The actual measurement device 200 has a moving mechanism 201, which relatively moves the probe P with respect to the object to be measured O placed on the mounting table 103. The moving mechanism 201 can be composed primarily of a cylindrical spindle, which is supported to be vertically movable by a support member and which has the probe P at the distal end thereof, a Z-direction drive mechanism which moves the spindle in the vertical direction, and an X-direction drive mechanism and a Y-direction drive mechanism which relatively move the mounting table 103 and the spindle in the directions which are orthogonal to the vertical direction and which are orthogonal to each other. Further, an air balance mechanism which generates, in the spindle, an upward force balancing the weight of the spindle including the probe P may be adopted as a part of the moving mechanism 201 or the actual measurement device 200. The probe P and the moving mechanism 201 are installed on the common stage 104 on which the X-ray source 101, the detector 102, and the mounting table 103 of the object to be measured O described above are disposed. In other words, the elements for acquiring the X-ray CT images and the elements for the three-dimensional shape measurement are combined on the single stage to constitute one measurement device. The three-dimensional coordinate axis in the device configuration is set as described above.

Further, the actual measurement device 200 has an input unit 202 which can be operated by an operator and a probe moving device 203 which moves the probe P in response to an operation input through the input unit 202. Further, the distal end of the probe P is provided with a pressure-sensitive sensor S. When the probe P is moved through the probe moving device 203 in response to an operation performed by the operator through the input unit 202 and comes in contact with the object to be measured O, the pressure-sensitive sensor S detects the contact, and the three-dimensional information of the position of the contact is detected. The detected three-dimensional position information of the object to be measured O is sent to the computer C or the like and processed. The probe moving device 203 is also composed of hardware, such as the computer C or the like, and software, such as a program, installed in the hardware. When a program for the probe moving device 203 is read into the computer C, various types of processing are carried out by an arithmetic processing unit, such as a CPU, and a storage unit, such as a memory.

The image correction device 300 corrects the X-ray CT image of the object to be measured O, which has been acquired by the image acquisition device 100, according to the three-dimensional shape of the object to be measured O actually measured by the actual measurement device 200. As illustrated in FIG. 11, the image correction device 300 has a display device 301 which displays, as sinograms, the data of the X-ray CT image acquired by the image acquisition device 100 and the data of the three-dimensional shape actually measured by the actual measurement device 200 on a display screen D, and the correction device 302 which reconstructs an image by using the ML-EM reconstruction method in the sequential approximate reconstruction method such that the sinogram of the X-ray CT image converges to the sinogram of the three-dimensional shape, thereby correcting the X-ray CT image. Each of the display device 301 and the correction device 302 is composed of hardware, such as the computer C, and software, such as a program installed in the hardware. When programs for the display device 301 and the correction device 302 are read into the computer C, various types of processing are carried out by an arithmetic processing unit, such as a CPU, and a storage unit, such as a memory.

Figure 14:
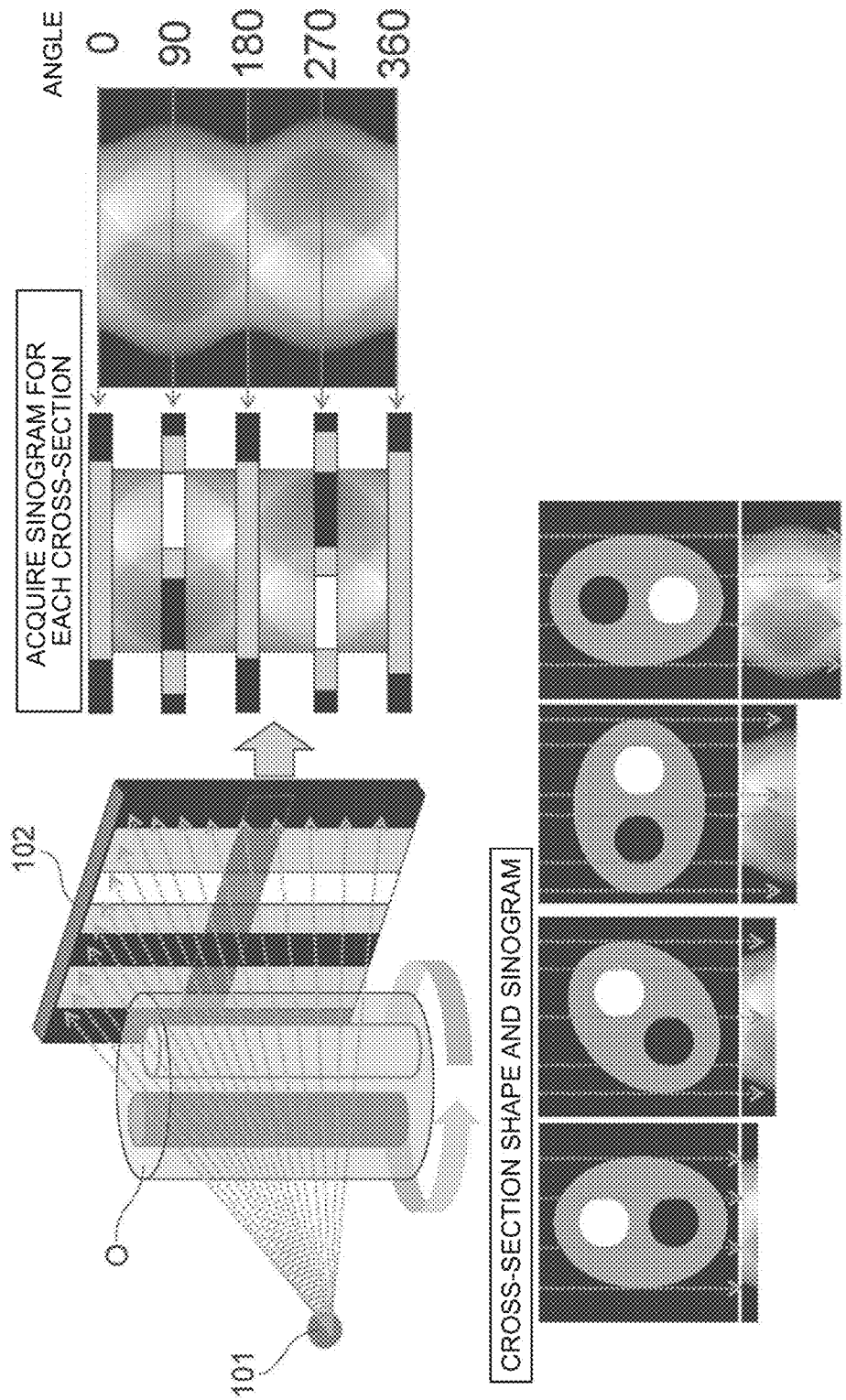
FIG. 14 presents diagrams for explaining the sinograms of an X-ray CT image of an object to be measured.
Figure 15:
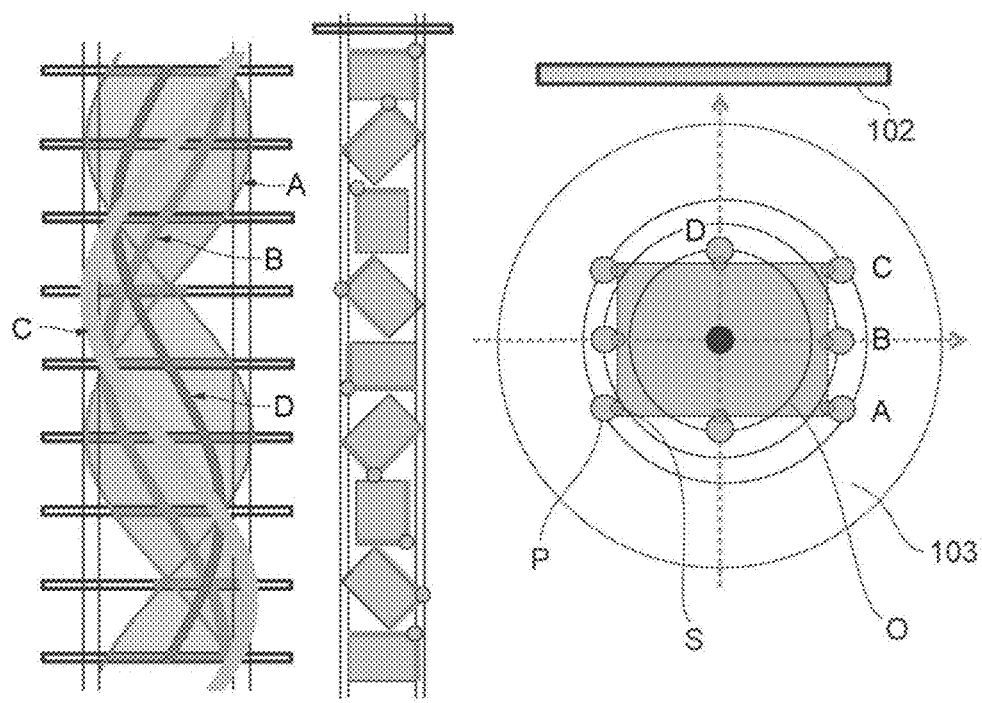
FIG. 15 presents diagrams for explaining the sinograms of the actual measurement data of the three-dimensional shape of an object to be measured.

Referring now to FIG. 14 and FIG. 15, the sinograms used for the image correction will be described. FIG. 14 presents explanatory diagrams for explaining the sinograms of the X-ray CT image of the object to be measured O, and FIG. 15 presents explanatory diagrams for explaining the sinograms of the actual measurement data of the three-dimensional shape of the object to be measured O. The sinogram is an image which represents, in the form of a sine wave, a detection signal for each angle when the object to be measured O is rotated by 360 degrees, and which is acquired for each section of the object to be measured O. The sinograms of the X-ray CT image (CT sinogram) at a predetermined section of the object to be measured O, which has an elliptical shape as observed in a planar view, acquired by the image acquisition device 100 are represented by the images as illustrated in, for example, FIG. 14. Further, the sinograms of the actual measurement data of the three-dimensional shape (actual measurement sinograms) at a predetermined section of the object to be measured O, which has a rectangular shape as observed in a planar view, actually measured by the actual measurement device 200 are represented by the images as illustrated in, for example, FIG. 15. Four sinograms A to D illustrated on the left side in FIG. 15 are the sinograms corresponding to edges A to D of the object to be measured O illustrated on the right side in FIG. 15. The edges of the object to be measured O are the points of contact between the pressure-sensitive sensor S of the probe P of the actual measurement device 200 and the object to be measured O.

Figure 16:
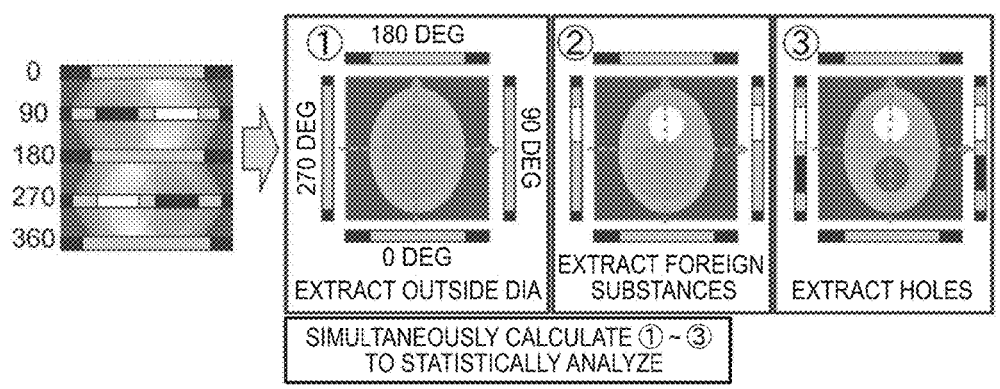
FIG. 16 presents diagram for explaining a maximum likelihood estimation and expectation-maximization reconstruction method.
Figure 17:
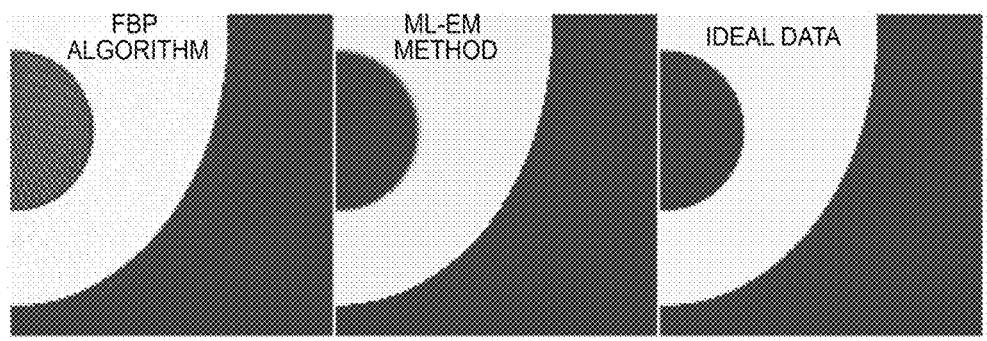
FIG. 17 presents diagrams illustrating the results of comparison between a section image reconstructed using the maximum likelihood estimation and expectation-maximization reconstruction method and a section image reconstructed using a filtered backprojection method.

Referring now to FIG. 16 and FIG. 17, the ML-EM reconstruction method used for image correction will be described. The ML-EM reconstruction method is a method in which calculation is repeated to determine an image that provides calculated projection data close to the measured projection data. It is assumed that projection data (sinograms) at 0°, 90°, 180° and 270° has been obtained, as illustrated in FIG. 16. At this time, the section images that will be obtained from the projection data can be estimated. For example, it is estimated from the outermost sinogram shape that the external shape is elliptical. Further, the sinograms of 90° and 270° suggest the presence of an extremely bright substance at an upper level of the ellipse and also the presence of an air layer at a lower level thereof. The sinograms of 180° and 270° exhibit no information on a substance inside the ellipse, so that it is presumed that the extremely bright substance and the air layer cancel each other. These procedures are simultaneously repeated to construct a consistent section image. This has outlined the ML-EM reconstruction method.

FIG. 17 illustrates the results of comparison between a section image reconstructed by using the ML-EM reconstruction method and a section image reconstructed by using the filtered backprojection method (hereinafter referred to as "the FBP method"). The presence of streak-like artifacts was observed in the section image reconstructed by the FBP method. It has also been found that the contrast differs between an opening in the specimen and the outer air layer. Meanwhile, such phenomena have not been observed in the one reconstructed by the ML-EM method, but a blurred profile of the opening has been observed. The FBP method is an effective reconstruction method for a specimen that contains elements having significantly different linear attenuation coefficients, but less effective for artifacts attributable to complicated shapes, such as a plate shape or a shape with many projections. This is because the FBP method uses a blur correction filter in reconstruction processing. In addition, other problems occur, such as emphasized edges or uneven contrasts, due to the influences of a correction filter. These problems lead to measurement errors, and the measurement errors may increase, depending on the shape of an object to be measured. Meanwhile, the ML-EM reconstruction method is capable of restraining the occurrence of artifacts manifested by the FBP method.

However, the ML-EM reconstruction method is a method designed to lead to a statistically most accurate image on the basis of projection data, so that it has been pointed out that the method poses the following three problems: (1) possible failure to converge because the ML-EM reconstruction method is a statistical method; (2) blurry edges of reconstructed images; and (3) an enormous volume of analysis with a resultant prolonged time required for the reconstruction. There has been a demand for developing a method that solves these problems in order to apply the ML-EM reconstruction method to practical use. We have solved the foregoing problems with the ML-EM reconstruction method by obtaining a correct sinogram which is created from the data obtained by actual measurement performed by a three-dimensional measurement unit, such as the actual measurement device 200 in the present embodiment, or an accurate cross-sectional image created from CAD data. Then, the entire image is corrected so as to converge to the sinogram.

Figure 18:
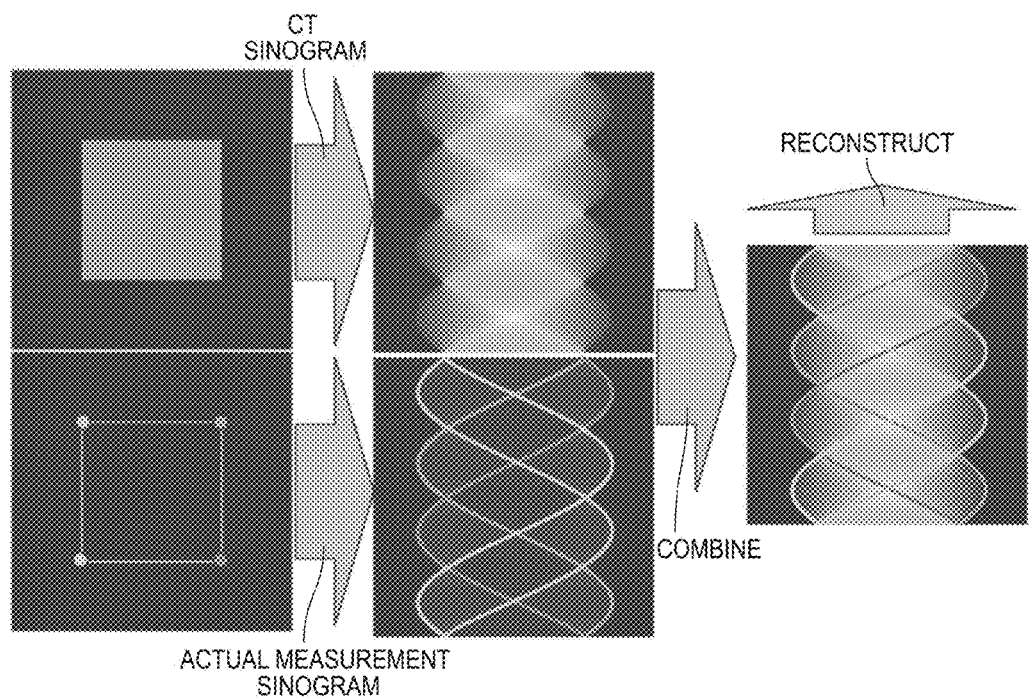
FIG. 18 presents diagrams for explaining a method for correcting an X-ray CT image by using the sinogram of the actual measurement data of a three-dimensional shape.

FIG. 18 is an explanatory diagram for explaining the method for correcting an X-ray CT image by using the sinograms of actual measurement data, i.e. the actual measurement sinogram, of a three-dimensional shape. The position of the probe P (the pressure-sensitive sensor S) of the actual measurement device 200 can be expressed by sine waves (sinogram). The X-ray CT image acquired by the image acquisition device 100 can be also expressed by sine waves (sinogram). In the present embodiment, the three-dimensional coordinate axis used in the actual measurement device 200 is the same as the three-dimensional coordinate axis used in the image acquisition device 100. This makes it possible to perfectly match the sinogram of the X-ray CT image (CT sinogram) with the sinogram of the actual measurement data obtained by the actual measurement device 200 (actual measurement sinogram). Thus, the convergence problem and the prolonged reconstruction time problem are solved by using the accurate sinogram of the external shape of the object to be measured O actually measured by the actual measurement device 200 to reconstruct the X-ray CT image by the ML-EM reconstruction method.

The X-ray three-dimensional measurement device 10 preferably has a vibration-proof function as the measures against vibrations from outside. Further, the X-ray three-dimensional device 10 is preferably shielded by a shielding member composed of lead, tungsten or the like, and the temperature and the humidity therein are preferably maintained constant by an air conditioner. Thus, when acquiring image information or the positional information on a three-dimensional shape, the influences of an external environment can be suppressed, allowing more accurate three-dimensional information to be obtained.

Figure 19:
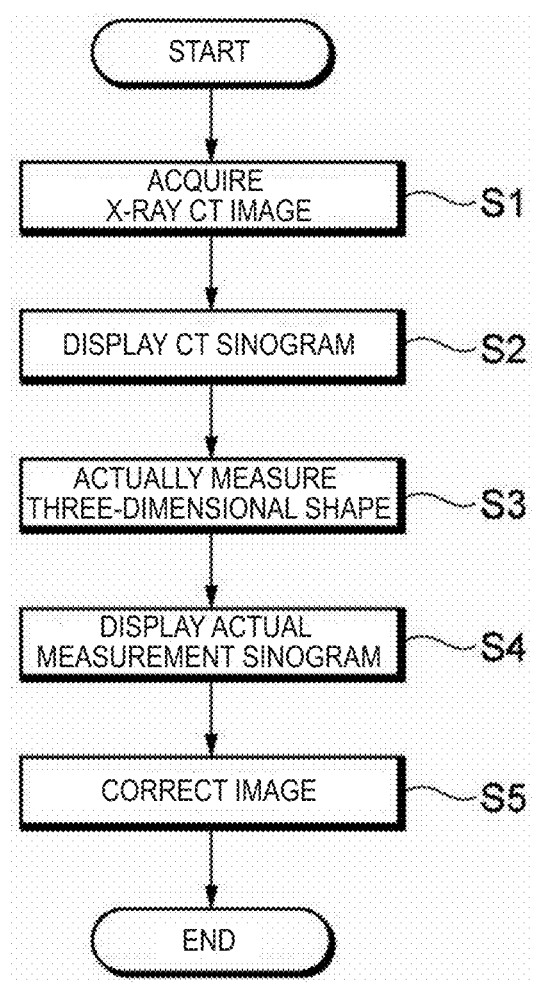
FIG. 19 is a flowchart illustrating the X-ray three-dimensional measurement method.

Referring now to the flowchart of FIG. 19 and also referring to FIG. 18 as necessary, a description will be given of the method for correcting the X-ray CT image of the object to be measured O by using the X-ray three-dimensional measurement device 10 according to the present embodiment.

First, the X-rays are applied to the object to be measured O from the X-ray source 101 of the image acquisition device 100 in order to detect the projection data at each rotational angle of the object to be measured O by the detector 102, thereby acquiring the X-ray CT image of the object to be measured O on a predetermined three-dimensional coordinate axis (image acquisition step S1). Then, the sinogram of the acquired X-ray CT image of the object to be measured O (the CT sinogram) is displayed on the display screen D by the display device 301, as illustrated in, for example, FIG. 18 (CT sinogram display step S2).

Then, the three-dimensional shape of the object to be measured O on the three-dimensional coordinate axis is actually measured by the actual measurement device 200 (actual measurement step S3). Next, the sinogram of the three-dimensional shape of the actually measured object to be measured O (actual measurement sinogram) is displayed on the display screen D by the display device 301 as illustrated in, for example, FIG. 18 (actual measurement sinogram display step S4). These actual measurement step S3 and actual measurement sinogram display step S4 may be carried out before the image acquisition step S1 and the CT sinogram display step S2.

Then, the image is reconstructed by using the ML-EM reconstruction method such that the CT sinogram is converged to the actual measurement sinogram thereby to correct the X-ray CT image (image correction step S5). At this time, as illustrated in FIG. 18, the image produced by merging the CT sinogram and the actual measurement sinogram can be displayed on the display screen D by the display device 301 to reconstruct the image.

The X-ray three-dimensional measurement device 10 according to the embodiment described above is capable of correcting the X-ray CT image of the object to be measured O on the predetermined three-dimensional coordinate axis by using the actual measurement values of the three-dimensional shape of the object to be measured O on the same coordinate axis. At this time, the sinogram of the three-dimensional shape of the object to be measured O actually measured by the actual measurement device 200 (the actual measurement sinogram) is defined as the correct sinogram, and the image is reconstructed by using the ML-EM reconstruction method such that the sinogram of the X-ray CT image (the CT sinogram) is converged to the correct sinogram thereby to correct the X-ray CT image, thus permitting the time required for the convergence (the time required for the reconstruction) to be shortened. This makes it possible to provide the advantage of the ML-EM reconstruction method (specifically, the advantage that permits reduced artifacts) while at the same time obviating the disadvantages of the ML-EM reconstruction method (specifically, the disadvantage of the statistical method that may fail to accomplish convergence, a blurry edge of a reconstructed image, and an enormous volume of analysis taking prolonged time for reconstruction).

The foregoing embodiments have illustrated the examples in which the contact type actual measurement device 200 using the probe P is adopted. Alternatively, however, a non-contact type actual measurement device using a laser, a CCD camera or the like may be adopted.

Further, the foregoing embodiments have illustrated the examples in which the sinogram of the actual measurement data of the three-dimensional shape of the object to be measured O, i.e. the actual measurement sinogram, is used to correct the X-ray CT image. Alternatively, however, a correct sinogram created using CAD data may be used in place of the actual measurement sinogram to correct the X-ray CT image. For example, CAD data may be subjected to voxel conversion and cross-section image conversion to create a correct sinogram, and the image may be reconstructed using the ML-EM reconstruction method such that the CT sinogram is converged to the correct sinogram, thereby correcting the X-ray CT image.

Further, the foregoing embodiments have illustrated the examples in which the X-ray CT image is corrected using the ML-EM reconstruction method. However, by converging a CT sinogram to an actual measurement sinogram, it is also possible to correct the X-ray CT image by using other reconstruction methods (e.g. the filtered backprojection method, the addition type ART method, the multiplication type ART method, the SIRT method, the gradient method, the steepest descent method, the conjugate gradient method, the MAP-EM method, and the convex method).

Further, the foregoing embodiments have illustrated the examples in which the X-ray CT image of the object to be measured O composed of a single material is corrected. However, the X-ray CT image of an object to be measured O composed of a plurality of materials can be also corrected at each energy. For example, if the specimen 2 in which two different metals, namely, the aluminum 21 and the iron 22, are scattered in the resin 20 is chosen as the object to be measured, as illustrated in FIG. 20, then the obtained characteristic X-ray peaks are first quantified by the signal processor 105. At this time, the peak intensities of the aluminum 21 and the iron 22 are quantified on the basis of preset energy threshold values that allow the aluminum 21 and the iron 22 to be distinguished from the resin 20 in the specimen 2. Thus, a transparent image of the aluminum 21 alone based on the spectrum quantified data between an upper limit value and a lower limit value and a transparent image of the iron 22 alone based on the spectrum quantified data that is larger than the upper limit value are acquired. In addition, a transparent image of the resin 20 is also acquired on the basis of the spectrum quantified data that is smaller than the lower limit value. Then, the image reconstruction device 106 carries out the reconstruction processing on each of the obtained transparent images to acquire the X-ray CT image for each energy, thereby obtaining the CT sinograms. Thereafter, the correct sinogram for each energy is created using CAD data or the like, and an image is reconstructed by the ML-EM reconstruction method such that the CT sinogram for each energy is converged to the corresponding correct sinogram thereby to correct the X-ray CT image for each energy.

The present invention is not intended to be limited to the embodiments described above, and modifications thereof obtained by those skilled in the art by adding design changes to the embodiments as appropriate are to be embraced in the scope of the present invention insofar as the modifications include the features of the present invention. In other words, the elements and the dispositions thereof, the materials, the conditions, the shapes, sizes and the like included in the embodiments are not limited to the illustrated ones and may be changed as appropriate. Further, the elements provided in the embodiments can be combined as long as the combinations are technically possible, and the combinations of the elements are to be embraced in the scope of the present invention insofar as the combinations of the elements include the features of the present invention.

REFERENCE SIGNS LIST 1, 1a, 1b X-ray source
2 Specimen to be imaged
20 Resin
21 Aluminum
22 Iron
3 Drive mechanism
4 Energy-dispersive detector
40 Sub-detector
5 CCD camera
50 Metal filter
51 Partition
10 X-ray three-dimensional measurement device
100 Image acquisition device
200 Actual measurement device
300 Image correction device
O Object to be measured
S1 Image acquisition step
S3 Actual measurement step
S5 Image correction step

What is claimed is:

1. A device for image reconstruction at different X-ray energies, comprising:
  an X-ray source that irradiates a specimen to be imaged with X-rays;
  an energy-dispersive detector that detects a characteristic X-ray emitted from the specimen to be imaged;
  a signal processor that quantifies the peak of the characteristic X-ray detected by the detector;
  an image reconstruction device that reconstructs an X-ray CT image at each of a plurality of energy levels on the basis of a signal from the signal processor; and
  an image correction device that corrects the X-ray CT image at each of the plurality of energy levels such that a sinogram of the X-ray CT image at each of the plurality of energy levels converges to a corresponding correct sinogram.

2. The device according to claim 1, wherein the detector includes a plurality of sub-detectors arranged in a line or panel formation.

3. The device according to claim 2, wherein the sub-detectors are detectors that acquire the characteristic X-ray coming from each element of the specimen to be imaged as a radiation energy spectrum by photon counting.

4. The device according to claim 1,
  wherein the detector acquires the characteristic X-ray coming from each element of the specimen to be imaged as a radiation energy spectrum, and
  the signal processor converts the peak of the characteristic X-ray of each element obtained from the radiation energy spectrum into quantified data for each element by threshold value processing.

5. The device according to claim 4, wherein the image reconstruction device reconstructs an image for each element of the specimen to be imaged on the basis of the quantified data of the characteristic X-ray peak of each element from the signal processor and combines the images into one image thereby to acquire a three-dimensional image that includes information from the elements of the specimen to be imaged.

6. The device according to claim 1, wherein the image reconstruction device uses a sequential approximate reconstruction algorithm.

7. The device according to claim 1, further comprising a drive mechanism that causes the specimen to be imaged, which is disposed between the X-ray source and the detector, to rotate and translationally move.

8. The device according to claim 1, further comprising a monitor that displays an image reconstructed by the image reconstruction device.

9. A method for image reconstruction at different X-ray energies, comprising the steps of:
   irradiating a specimen to be imaged with X-rays;
   detecting a characteristic X-ray emitted from the specimen to be imaged by an energy-dispersive detector;
   quantifying a peak of the detected characteristic X-ray;
   reconstructing an X-ray CT image at each of a plurality of energy levels on the basis of quantified data of the characteristic X-ray peak; and
   correcting the X-ray CT image at each of the plurality of energy levels such that a sinogram of the X-ray CT image at each of the plurality of energy levels converges to a corresponding correct sinogram.

* * * * *